United States Patent
Harrison

(10) Patent No.: US 6,523,540 B1
(45) Date of Patent: Feb. 25, 2003

(54) SPERMICIDAL LUBRICATED POLYURETHANE CONDOMS

(75) Inventor: Michael J. Harrison, Princeton, NJ (US)

(73) Assignee: Carter-Wallace, Inc., DE (US)

( * ) Notice: Subject to any disclaimer, the term of this patent is extended or adjusted under 35 U.S.C. 154(b) by 0 days.

(21) Appl. No.: 09/267,250

(22) Filed: Mar. 12, 1999

(51) Int. Cl.$^7$ .................................................. A61F 6/04
(52) U.S. Cl. ...................................... 128/844; 128/918
(58) Field of Search .............................. 128/842, 844, 128/918; 604/347–353

(56) References Cited

U.S. PATENT DOCUMENTS 5,284,158 A * 2/1994 Mallette ..................... 128/844
5,490,519 A * 2/1996 Hessel ........................ 128/844
5,623,946 A * 4/1997 Hessel ........................ 128/844

* cited by examiner

Primary Examiner—Michael A. Brown
(74) Attorney, Agent, or Firm—Kevin B. Clarke, Esq.

(57) ABSTRACT

The present invention relates to improved condoms which in addition to providing protection against the transmission of disease and pregnancy also allow for a high degree of stimulation and sensitivity during sexual intercourse. The condoms comprise thin, soft, strong polyether polyol and polyester polyol diisocyanate based polyurethane elastomers in combination with a spermicidal lubricant.

18 Claims, 1 Drawing Sheet

SPERMICIDAL LUBRICATED POLYURETHANE CONDOMS

FIELD OF THE INVENTION

This invention relates to the field of condoms which are effective contraceptives and provide reliable protection against sexually transmitted diseases. More particularly, the present invention relates to spermicidally lubricated polyether polyol aliphatic diisocyanate based polyurethane elastomer condoms.

DESCRIPTION OF THE PRIOR ART

Rubber latex condoms, both dry and lubricated, have been available for many years. Among the advantages of presently available rubber latex condoms are their relative freedom from side effects to either partner, their low cost and their simplicity of use.

However, the rubber latex condoms have disadvantages such as breakage, leakage and slippage, especially in those cases where thinner materials are used in condom production in order to facilitate increased tactile sensation and heat transference. In such cases, the use of thinner condoms may entail a considerable increase in risk since the thinner condoms may not have adequate tensile strength and break force properties which are necessary to withstand the rigors of robust sexual intercourse.

In order to overcome the disadvantages of rubber latex condoms, it has been proposed to produce condoms from polyurethane elastomers which do not suffer from the undesirable film thickness and inherent insulating characteristics which result in inefficient heat transfer and reduction in sensory perception to the user, which are characteristic of natural rubber latex based condoms.

In general, polyurethane elastomers are polymers produced by the reaction of diisocyanates and polymeric di-hydroxy functional alcohols known as polyols. Polyurethane elastomers are regarded as block copolymers. The highly chemically reactive diisocyanates join the polyols together with a urethane linkage.

Polyols used to form polyurethane elastomers are obtained from two chemically distinct classes: polyether polyols and polyester polyols, the latter including polycaprolactones. For elastomer synthesis, both polyols are available in various molecular weights; products in the 600 to 3000 molecular weight range are commonly used industrially.

The most commonly used polyether polyols are the polypropylene glycols and the polytetramethylene glycols. The polyester polyols are prepared by the reaction of dibasic acids (usually adipic acid) with numerous different diols such as ethylene glycol, 1,2-propylene glycol, diethylene glycol, etc. Currently, polyester polyols are more extensively used for polyurethane elastomer production than are the polyether polyols.

The isocyanates used for elastomer production are generally bi-functional. These diisocyanates can be based on either aromatic or aliphatic structural backbones. An example of an aromatic diisocyanate used for elastomer production is 4,4'-diphenylmethane diisocyanate. An example of an aliphatic diisocyanate used for elastomer production is 4,4'-dicyclohexylmethane diisocyanate.

It is well established that strongly ionic solvents, such as alcohols, can quickly disrupt the molecular chain structure of polyurethanes, leading to a rapid fall in physical properties. In fact, many materials, both relatively ionic and non-ionic, can cause similar disruptions due to the varying morphology and chemistry of these polymers.

Nonoxynol-9 is the active agent in most spermicidal products that are available in the United States. These products include condoms, foams, jellies, creams, suppositories, tablets, etc. Two other spermicides approved for use in the United States are octoxynol and Nonoxynol-11. All three materials can be classified as non-ionic ethoxy-based surfactants that kill sperm by destroying the cell membrane. Other surfactant products, including menfegol and benzalkonium chloride, are widely used as spermicides in other parts of the world.

Spermicides are usually used in conjunction with a base which can act as both a sexual lubricant and carrier for the spermicide.

Non-spermicidal condom lubricants, such as silicone fluids, aqueous systems and poly(alkoxy) glycols such as polyethylene glycol mol. wt. 400, available commercially as PEG 400, are currently used extensively throughout the natural rubber latex condom industry and also act as carriers for the spermicide.

In the U.S., Nonoxynol-9 is used almost exclusively in spermicidally lubricated condom products. Therefore, compatibility of Nonoxynol-9 with polyurethanes is essential if a spermicidally lubricated polyurethane condom is to be successfully developed and marketed.

THE PRESENT INVENTION

Figures 1, 2:
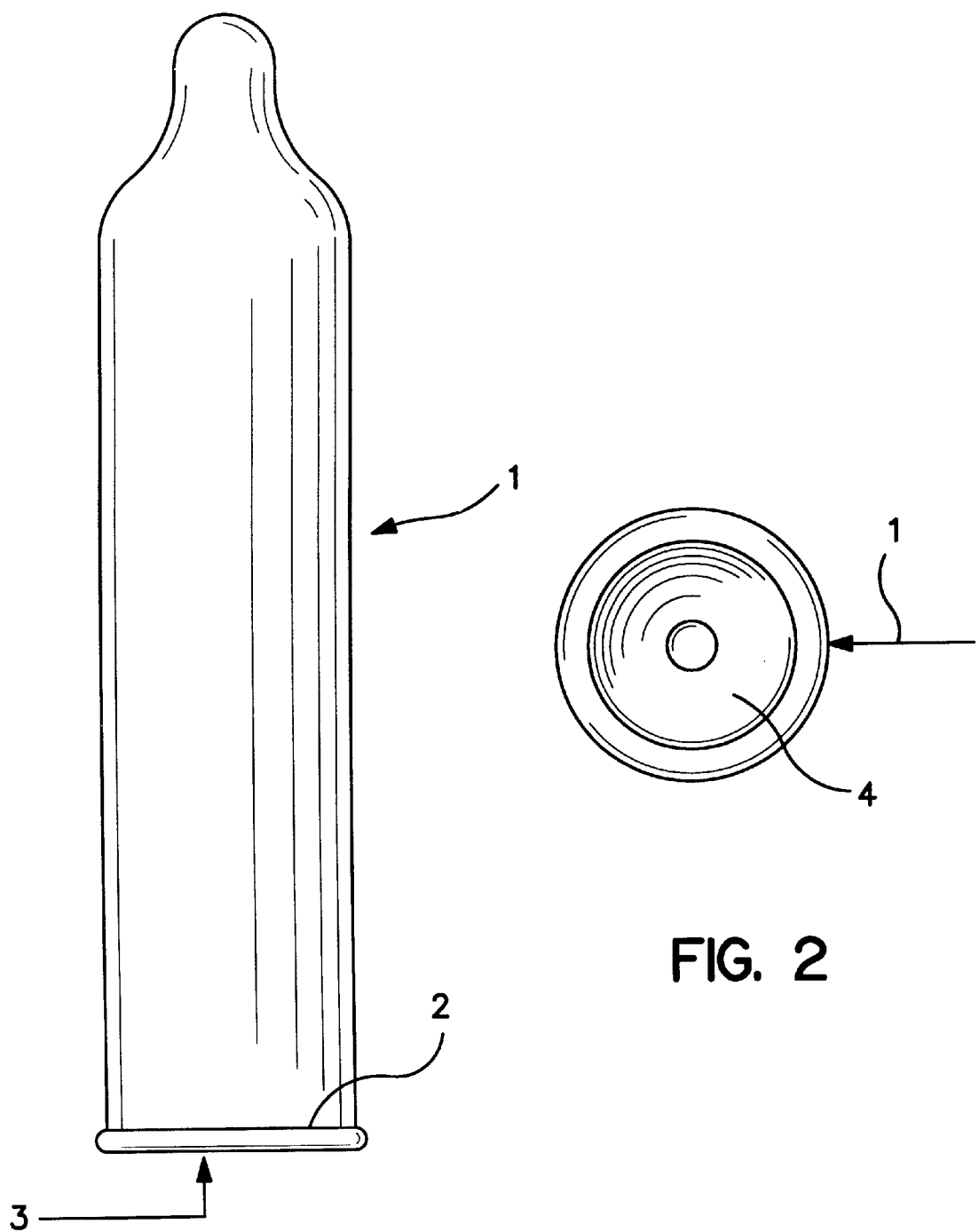
FIG. 1 is a perspective view of a condom suitable for use in the present invention.
FIG. 2 is an elevational view of the cup through the open end of a rolled condom suitable for application of the spermicides of the invention.

As noted above, it is well established that strongly ionic solvents, such as alcohols, quickly disrupt the molecular chain structure of polyurethanes. In fact, Nonoxynol-9, the USP monographed spermicide of choice in the U.S., is also used as a plasticizer for polyurethanes. If too much plasticizer is added to a polymer, it can weaken any resultant film to a point where it cannot be utilized for its intended use.

In accordance with the present invention, it has been found that polyether polyol aliphatic diisocyante based polyurethane elastomers can be combined with non-ionic ethoxy-based spermicides without destruction of the chain structure of the polyurethane.

As part of the present invention, an evaluation of various chemically distinct polyurethane elastomers in contact with spermicidal lubricants was undertaken.

For purposes of the present invention, polyurethanes are divided into two chemically distinct classes, namely: polyester-based (including caprolactones) and polyether-based polyurethanes. Since it is intended to produce a condom from elastomers, the evaluation was confined to this category of polyurethanes. Other categories of polyurethanes not forming a part of the present invention include foams, coatings, rigid films, etc.

Polyurethanes are produced by a chemical reaction between mutually reactive monomers. For elastomers, these monomers are specifically: di-hydroxy polyesters or polyethers, commonly known as polyols, and diisocyanates which can be based on either aromatic or aliphatic structural backbones. The reaction between a hydroxy group and an isocyanate group produces a urethane group. These mutually reactive bifunctional monomers produce long linear chains via urethane groups, which are termed polyurethanes and, specifically in the case of the present invention, polyurethane elastomers. The study design for evaluating combinations with a wide range of polyurethane elastomers is given in Table 1.

TABLE 1

POLYOL and DIISOCYANATE COMBINATIONS

| POLYOLS | DIISOCYANATE | |
| --- | --- | --- |
| | Aliphatic Diisocyanate | Aromatic Diisocyanate |
| Polyether Polyol | X | X |
| Polyester Polyol | X | X |

LEGEND
X = example was evaluated
Aliphatic diisocyanate = 4,4'-dicyclohexylmethane diisocyanate
Aromatic diisocyanate = 4,4'-diphenylmethane diisocyanate
Polyether polyol = polytetramethylene glycol (mol. wt. 2000)
Polyester polyol = poly(alkylene) adipates As noted previously, the spermicide of choice for condoms in the United States is Nonoxynol-9. Other materials approved in the United States as spermicides are Octoxynol and Nonoxynol-11. Both of these materials are chemically very similar to Nonoxynol-9. All three materials can be classified as non-ionic ethoxy-based surfactants.

The lubricant acts as a carrier for the spermicide and also provides some lubricity during coitus. Commonly used bases are: aqueous gels, silicones and poly (alkoxy) glycols such as polyethylene glycol mol. wt. 400 or PEG 400.

The spermicidal lubricant of choice for the polyurethane condoms of the present invention is 8% w/w Nonoxynol-9 in PEG 400.

Samples of four chemically distinct polyurethane elastomers were obtained, see Table 1. Films from each, in the appropriate condom thickness range, were produced using solvent solution dipping. Test pieces cut from these films were totally immersed in each of three spermicidal lubricant types: aqueous, silicone and PEG-based. One set of test pieces were exposed for seven days at room temperature and another set at 70° C. for seven days. This was considered a gross exposure; however, it clearly defines any compatibility problems between lubricant and polymer. Changes in the tensile properties of the films were used to characterize any deterioration in material integrity.

Spermicidal aqueous-based lubricant caused no significant deterioration in solvent cast films of the polyurethanes studied. The PEG 400-based spermicidal lubricant is compatible with polyurethanes made using aliphatic diisocyanate monomers, but is incompatible with polyurethanes made from aromatic diisocyanate monomers. The spermicidal silicone-based lubricant has little or limited compatibility with the range of polyurethanes evaluated.

Example 1, which follows, was undertaken in order to determine the effect of the gross exposure of various spermicidal condom lubricants on the tensile properties of polyurethane elastomers.

Thin films of each type of polyurethane were produced by dip coating glass mandrels in a polymer/THF solution and then driving off the solvent with heat. Dumbbell test pieces cut from these films were immersed in the various bulk spermicidal lubricants. These samples were stored at room temperature and 70° C. for seven days after which time a tensile strength determination was undertaken on each dumbbell.

The immersion of the test pieces in bulk lubricant (15 to 25g) represents a gross exposure. Using this method, the gross effect of the lubricants on the physical properties of the condom material was evaluated. Consider that less than 1.2g of lubricant is to be used in packaged commercial products. This, therefore, provides a wide safety margin for a condom in use.

The storage condition of 70° C. for seven days is an accelerated aging test derived from the latex condom standard ASTM D3294-89. It is considered a severe test for the packed product; note that it is designed as a challenge for this product.

EXAMPLE 1

Examples of each of the four types of polyurethanes described in Table 1 were sourced as follows:
Polyether Polyol Aliphatic Diisocyanate
  Tecoflex SG-80A, Lot L010-02854 from Thermedics Inc.
Polyether Polyol Aromatic Diisocyanate
  Tecothane TT-1085A, Lot E999-02699 from Thermedics Inc.
Polyester Polyol Aliphatic Diisocyanate
  Experimental resin from Thermedics Inc.
Polyester Polyol Aromatic Diisocyanate
  Estane 5710F5P, Lot 6799100 from B.F. Goodrich 1. A dip solution was prepared for each polymer at approximately 10% w/w in THF.
2. Any polymer gels were removed, if required, by filtering the solution through a cotton cheesecloth.
3. Glass mandrels were dipped twice and dried, and then stripped or removed from the mandrels aided by a dusting agent.
4. The target thickness for the films was 35 to 60 microns.
5. Dumbbell test pieces, ASTM Type C, were cut from each of the polymers.
6. The thickness of each dumbbell was determined using the method in ASTM D-412 and numbered for reference.
7. Each test piece was then placed in a numbered glass vial (25 ml) and lubricant was added to fill capacity.
8. The glass vials were then stored either at room temperature or 70° C. for one week.
9. At the completion of the storage time, each dumbbell was removed just prior to tensile testing. Excess lubricant was removed with absorbent paper tissue to prevent slippage of the dumbbell in the grips of the tensile test machine.

10. Aqueous-based, polyethylene glycol-based and silicone-based spermicidal condom lubricants were evaluated in this study.

11. The tensile strength was determined according to the methods in Physical Testing Laboratory Procedure 160-3A.

A summary of tensile strength data for each type of polyurethane exposed to the spermicidal condom lubricants follows:

POLYETHER POLYOL ALIPHATIC DIISOCYANATE POLYURETHANE

The PEG 400 and aqueous-based spermicidal lubricants are stable with this film.

The film, after exposure to the silicone-based lubricant degraded after seven days at 70° C., but is unaffected at RT. This suggests that the lubricant breaks down releasing Nonoxynol-9 at 70° C. Nonoxynol-9 is a plasticizer or softener for polyurethanes in general. If excessive amounts are placed into a polyurethane film, a complete breakdown in the integrity of the material will occur.

The effect of the PEG 400-based lubricant on the tensile properties is the benchmark since it has been shown that this product has satisfactory performance in use and good shelf life. Using this reference, it is clear that the aqueous-based lubricant, as well as the PEG 400-based, will provide a stable product but that the silicone-based lubricant will be an unstable product.

POLYETHER POLYOL AROMATIC DIISOCYANATE

With this material, only the aqueous-based lubricant was acceptable. The silicone and PEG-based lubricant caused considerable deterioration to the tensile properties of the films, even at room temperature.

POLYESTER POLYOL ALIPHATIC DIISOCYANATE POLYURETHANE

The tensile strength results show that the only lubricant to have any serious detrimental effect on the tensile strength of the material was the silicone-based system after seven days at 70° C.

POLYESTER POLYOL AROMATIC DIISOCYANATE

As with the polyether polyol aromatic diisocyanate, the only lubricant which did not severely affect the tensile properties of films made from this material was the aqueous-based system.

The spermicidal aqueous-based lubricant caused no significant deterioration in the films of any of the polyurethane types tested. Even after aging at 70° C. for seven days, the tensile properties of all the films remained high. While not being bound by any theory, this could be attributed to an equilibrium being established between the polyurethane, a solid phase, and the aqueous lubricant, a liquid phase, to such a degree that the level of Nonoxynol-9 entering the polymer is not enough to cause significant deterioration in the integrity of the film.

The polyethylene glycol-based system is also believed to establish an equilibrium of the Nonoxynol-9 between the lubricant and the different types of polyurethane. However, it is clear that the equilibrium is variable since significant deterioration has occurred in two types of polyurethane, even at room temperature. The film integrity of the polyurethane made using aromatic diisocyanate was completely destroyed, and the polyester polyol aromatic diisocyanate material actually dissolved. The polyurethanes made from an aliphatic diisocyanate remain relatively stable even at 70° C. for seven days. The reason for this difference has yet to be resolved.

In terms of compatibility, the worst product is the silicone-based lubricant. Significant deterioration is seen with most of the polyurethanes and particularly after storage at 70° C. for seven days. The stability of the lubricant at this temperature is open to question.

In summary, spermicidal aqueous-based lubricant cause no significant deterioration in solvent cast films of this range of polyurethanes. The PEG 400-based spermicidal lubricant is compatible with polyurethanes made using aliphatic diisocyanates monomers, but is incompatible with polyurethanes made from aromatic diisocyanates monomers. The spermicidal silicone-based lubricant has little or limited compatibility with the range of polyurethanes evaluated.

Polyether polyol aliphatic diisocyanate elastomers containing Nonoxynol-9 as a spermicide is the preferred combination of the present invention.

The preferred elastomers of the present invention are linear chain, aliphatic polyether-based polyurethanes, which are synthesized from the solid phase polymerization reaction of methylene bis(4-cyclohexylisocyanate) and polytetramethylene ether glycol of about 2000 molecular weight which is chain extended/terminated with 1,4-butanediol. The elastomers are clear and because of their aliphatic nature will not yellow upon aging nor upon exposure to oxygen or ultraviolet light.

The polyurethane elastomers are dissolved in a solvent preferably tetrahydrofuran in order to prepare the dip solution for condom manufacture. The only other additive to the dip solution, at a very low level, is a mold release agent such as a silicone fluid (polydimethylsiloxane-polyoxyethylene copolymer) which will facilitate removal of the formed condom from the mandrels.

Example 2, which follows, sets forth a polyurethane condom formulation for use in the present invention.

EXAMPLE 2

| Ingredient | w/w |
| --- | --- |
| Tetrahydrofuran | 89.45% |
| Polyether polyol aliphatic diisocyanate | 10.53% |
| Silicone fluid | 0.02% |
| | 100.00% |

A preferred method for manufacturing the polyurethane elastomer condoms of the present invention is fully described in copending commonly assigned U.S. patent application Ser. No. 09/095,330 filed Jun. 10, 1998.

The primary process in the manufacture of the polyurethane elastomer condom is the condom forming or dipping process. The following are the process control parameters for the dipping process:

| | |
|---|---|
| Dipping Chamber Atmosphere | Temperature 50–70° F., Filtered (maximum 100 mM mesh) recirculating nitrogen atmosphere. |
| Dip Tank | Temperature 50–55° F. controlled by passing recirculated dipping solution through a heat exchanger system; Viscosity 100–300 cps (depending upon molecular weight distribution of the polymer) controlled by automated viscometer system on closed loop from feed and dip tanks; the automated dipping solution level control system provides control of particulate matter and maintains viscosity and temperature uniformity of the dip solution which is recirculated at 40–50 gallons per minute through a 25–50 mM bag-type filter. |
| Film Drying Station 1 | Temperature 90–115° F., air flow approximately 1000 F/M (feet per minute) filtered (maximum 100 mM mesh) recirculating nitrogen atmosphere. |
| Film Drying Station 2 | Temperature 135–152° F., air flow approximately 1000 F/M filtered (maximum 100 mM mesh) recirculating nitrogen atmosphere. |
| First Chill Station | Temperature 50–55° F., air flow approximately 750 F/M filtered (maximum 100 mM mesh) recirculating nitrogen atmosphere. |
| Second Chill Station | Temperature 45–50° F., air flow approximately 750 F/M filtered (maximum 100 mM mesh) recirculating nitrogen atmosphere. |
| Third Chill Station | Temperature 30–40° F., air flow approximately 750 F/M filtered (maximum 100 mM mesh) recirculating nitrogen atmosphere. |

The dipping section of the manufacturing equipment operates as noted above in a nitrogen gas environment that is isolated from the cleaning/take-off section of the dipping line by means of an air lock. This air lock not only minimizes infiltration of oxygen in the dipping section of the line but also aids in controlling particulate matter. A cover on the dip tank also helps to prevent any contamination. THF that evaporates from the dip tank and mandrels is recovered for re-use. An in-line analyzer monitors water and stabilizer content of the recovered THF for suitability prior to re-use.

The second section of the condom production line is composed of the condom take-off and form cleaning section. The process control parameters are as follows:

| | |
|---|---|
| Former Wash Station | Temperature up to 160° F.; wash solution is recirculated through a 25–50 mM bag-type filter. |
| Former Rinse Station | Temperature up to 160° F.; rinse solution is recirculated through a 25–50 mM bag-type filter. |
| Former Drying Oven | Temperature 160° F.; air flow approximately 1000 F/M filtered (maximum 100 mM mesh) recirculated air. |

The condoms 1 are then rolled around the ring to form a cup-shaped elastic ring 2 of predetermined size and circumference. The result is several layers of polyurethane elastomer being rolled around the thickened ring formed at the top, open end 3 of the sheath forming a cup 4 within the circumference of the ring. In this form, the condom is easily mountable for use during sexual intercourse and lubricants and spermicides may be added to the cup-shaped polyurethane elastomer sheath.

Example 3 illustrates a preferred spermicide/lubricant formulation for use in the present invention.

| Ingredient | W/W |
|---|---|
| Polyethylene glycol, Mol. Wt. 400 | 92.00% |
| Nonoxynol-9 | 8.00% |
| | 100.00% |

TABLE 2

| | DATA LOCATION | |
|---|---|---|
| TYPE OF POLYURETHANE | SUMMARY OF DATA | EXPERIMENTAL DATA |
| 1. Polyether polyol aliphatic diisocyanate | Table 3 | Appendix No. 4 |
| 2. Polyester polyol aliphatic diisocyanate | Table 4 | Appendix No. 5 |
| 3. Polyether polyol aromatic diisocyanate | Table 5 | Appendix No. 6 |
| 4. Polyester polyol aromatic diisocyanate | Table 6 | Appendix No. 7 |

NOTE: References for laboratory notebooks for the experimental data can be found in the respective appendices.

TABLE 3

EFFECT of SPERMICIDAL CONDOM LUBRICANT on a
POLYETHER POLYOL ALIPHATIC DIISOCYANATE POLYURETHANE

| STORAGE TEMPERATURE (7 days) | SPERMICIDAL LUBRICANT | THICKNESS (mm) | TENSILE (MPa) | BREAK (N) | ELONGATION (%) |
|---|---|---|---|---|---|
| Room Temperature | DRY | 0.046 | 51.20 | 14.07 | 635 |
| Room Temperature | Polyethylene glycol-based | 0.049 | 48.44 | 14.03 | 685 |
| Room Temperature | Aqueous-based | 0.047 | 46.02 | 12.87 | 700 |
| Room Temperature | Silicone-based | 0.048 | 41.81 | 11.94 | 690 |
| 70° C. | DRY | 0.049 | 51.42 | 15.07 | 710 |

TABLE 3-continued

EFFECT of SPERMICIDAL CONDOM LUBRICANT on a
POLYETHER POLYOL ALIPHATIC DIISOCYANATE POLYURETHANE

| STORAGE TEMPERATURE (7 days) | SPERMICIDAL LUBRICANT | THICKNESS (mm) | TENSILE (MPa) | BREAK (N) | ELONGATION (%) |
|---|---|---|---|---|---|
| 70° C. | Polyethylene glycol-based | 0.050 | 45.25 | 13.69 | 810 |
| 70° C. | Aqueous-based | 0.045 | 43.85 | 11.91 | 917 |
| 70° C. | Silicone-based | 0.050 | 13.38 | 4.00 | 630 |

TABLE 4

EFFECT of SPERMICIDAL CONDOM LUBRICANT on a
POLYETHER POLYOL ALIPHATIC DIISOCYANATE POLYURETHANE

| STORAGE TEMPERATURE (7 days) | SPERMICIDAL LUBRICANT | THICKNESS (mm) | TENSILE (MPa) | BREAK (N) | ELONGATION (%) |
|---|---|---|---|---|---|
| Room Temperature | DRY | 0.059 | 61.12 | 21.54 | 395 |
| Room Temperature | Polyethylene glycol-based | 0.057 | 57.65 | 19.90 | 415 |
| Room Temperature | Aqueous-based | 0.059 | 53.87 | 19.09 | 405 |
| Room Temperature | Silicone-based | 0.057 | 54.62 | 18.62 | 425 |
| 70° C. | DRY | 0.057 | 59.47 | 20.22 | 395 |
| 70° C. | Polyethylene glycol-based | 0.058 | 35 | 18.32 | 530 |
| 70° C. | Aqueous-based | 0.060 | 49.70 | 17.94 | 475 |
| 70° C. | Silicone-based | 0.059 | 48.29 | 17.00 | 675 |

TABLE 5

EFFECT of SPERMICIDAL CONDOM LUBRICANT on a
POLYETHER POLYOL AROMATIC DIISOCYANATE POLYURETHANE

| STORAGE TEMPERATURE (7 days) | SPERMICIDAL LUBRICANT | THICKNESS (mm) | TENSILE (MPa) | BREAK (N) | ELONGATION (%) |
|---|---|---|---|---|---|
| Room Temperature | DRY | 0.040 | 68.80 | 16.51 | 560 |
| Room Temperature | Polyethylene glycol-based | 0.039 | 40.00 | 9.45 | 698 |
| Room Temperature | Aqueous-based | 0.037 | 61.19 | 13.46 | 579 |
| Room Temperature | Silicone-based | 0.038 | 33.10 | 7.53 | 611 |
| 70° C. | DRY | 0.041 | 72.17 | 17.78 | 590 |
| 70° C. | Polyethylene glycol-based | 0.038 | 4.94 | 1.10 | 800 |
| 70° C. | Aqueous-based | 0.036 | 57.02 | 12.61 | 718 |
| 70° C. | Silicone-based | 0.036 | 9.26 | 1.99 | 607 |

TABLE 6

EFFECT of SPERMICIDAL CONDOM LUBRICANT on a
POLYETHER POLYOL AROMATIC DIISOCYANATE POLYURETHANE

| STORAGE TEMPERATURE (7 days) | SPERMICIDAL LUBRICANT | THICKNESS (mm) | TENSILE (MPa) | BREAK (N) | ELONGATION (%) |
|---|---|---|---|---|---|
| Room Temperature | DRY | 0.048 | 85.44 | 24.87 | 500 |
| Room Temperature | Polyethylene glycol-based | | samples dissolved | | |
| Room Temperature | Aqueous-based | 0.051 | 59.56 | 18.09 | 540 |
| Room Temperature | Silicone-based | 0.054 | 22.79 | 7.40 | 585 |
| 70° C. | DRY | 0.051 | 76.22 | 23.35 | 535 |
| 70° C. | Polyethylene glycol-based | | samples dissolved | | |
| 70° C. | Aqueous-based | 0.052 | 43.74 | 13.66 | 645 |
| 70° C. | Silicone-based | 0.053 | 3.61 | 1.16 | 380 |

I claim:

1. A condom formed of a polyurethane elastomer composition selected from one of the group consisting of polyether polyol and polyester polyol aromatic or aliphatic diisocyanate-based polyurethanes in combination with a spermicidal aqueous-based lubricant.

2. A condom according to claim 1 wherein said polyurethane elastomer is produced by the reaction of a polyester polyol and an aromatic diisocyanate.

3. A condom according to claim 2 wherein said polyester polyol is produced by the reaction of a dibasic acid and a diol.

4. A condom according to claim 2 wherein said aromatic diisocyanate is 4,4'-diphenylmethane diisocyanate.

5. A condom according to claim 1 wherein said polyurethane elastomer is produced by the reaction of a polyether polyol and an aromatic diisocyanate.

6. A condom according to claim 5 wherein said polyether polyol is a polypropylene glycol.

7. A condom according to claim 5 wherein said polyether polyol is a polytetramethylene glycol.

8. A condom according to claim 1 wherein said spermicidal lubricant is nonoxynol-9 in an aqueous carrier.

9. A condom according to claim 1 wherein said polyurethane elastomer is produced by the reaction of a polyester polyol and an aliphatic diisocyanate.

10. A condom according to claim 9 wherein said polyester polyol is a polyalkylene adipate.

11. A condom according to claim 10 wherein said polyether polyol is polypropylene glycol.

12. A condom according to claim 11 wherein said polyether polyol is polytetramethylene glycol.

13. A condom according to claim 9 wherein said aliphatic diisocyanate is 4,4'-diclyclohexylmethane diisocyanate.

14. A condom according to claim 10 wherein said aliphatic diisocyanate is 4,4'-diclyclohexylmethane diisocyanate.

15. A condom according to claim 1 wherein said polyurethane elastomer is produced by the reaction of a polyether polyol and an aliphatic diisocyanate.

16. A condom formed of a polyurethane elastomer composition selected from one of the group consisting of polyether polyol and polyester polyol aliphatic diisocyanate based polyurethanes in combination with a spermicidal poly(alkoxy) glycol-based lubricant.

17. A condom according to claim 1 wherein said spermicidal lubricant is nonoxynol-9 in a carrier consisting essentially of poly(alkoxy) glycols.

18. A condom according to claim 17 wherein said poly(alkoxy) glycol is a polyethylene glycol having a molecular weight of approximately 400.

* * * * *